US008986207B2

(12) United States Patent
Li et al.

(10) Patent No.: US 8,986,207 B2
(45) Date of Patent: Mar. 24, 2015

(54) SYSTEMS AND METHODS FOR PROVIDING SENSOR ARRAYS FOR DETECTING PHYSIOLOGICAL CHARACTERISTICS

(75) Inventors: Youzhi Li, Longmont, CO (US); Bo Chen, Louisville, CO (US); Edward M. McKenna, Boulder, CO (US); Paul Stanley Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 531 days.

(21) Appl. No.: 12/944,955

(22) Filed: Nov. 12, 2010

(65) Prior Publication Data

US 2011/0112379 A1 May 12, 2011

Related U.S. Application Data

(60) Provisional application No. 61/260,743, filed on Nov. 12, 2009.

(51) Int. Cl.
| | |
|---|---|
| *A61B 5/00* | (2006.01) |
| *A61B 5/1455* | (2006.01) |
| *A61B 5/0205* | (2006.01) |
| *G06F 19/00* | (2011.01) |

(Continued)

(52) U.S. Cl.
CPC ........... *A61B 5/14552* (2013.01); *A61B 5/0205* (2013.01); *G06F 19/345* (2013.01); *A61B 5/72* (2013.01); *A61B 5/14551* (2013.01); *A61B 5/7221* (2013.01); *A61B 5/7264* (2013.01); *G06F 19/3406* (2013.01); *G06F 19/3487* (2013.01); *G06F 19/34* (2013.01); *A61B 5/6804* (2013.01); *A61B 5/02416* (2013.01); *A61B 5/0816* (2013.01); *A61B 5/726* (2013.01); *A61B 2562/0233* (2013.01); *A61B 2562/046* (2013.01); *Y10S 128/92* (2013.01); *Y10S 128/925* (2013.01)
USPC ............. 600/301; 600/323; 600/483; 706/15; 128/920; 128/925

(58) Field of Classification Search
CPC ... G06F 19/34; G06F 19/345; G06F 19/3406; G06F 19/3487; A61B 5/02; A61B 5/0205; A61B 5/14551; A61B 5/72; A61B 5/7221; A61B 5/7264
See application file for complete search history.

(56) References Cited

U.S. PATENT DOCUMENTS

| | | |
|---|---|---|
| 5,626,140 A | 5/1997 | Feldman et al. |
| 6,599,251 B2 | 7/2003 | Chen et al. |

(Continued)

FOREIGN PATENT DOCUMENTS

WO     WO 03009754 A1 * 2/2003

*Primary Examiner* — William Thomson
*Assistant Examiner* — Marie Archer
(74) *Attorney, Agent, or Firm* — Shvarts & Leiz LLP

(57) ABSTRACT

Systems and methods for determining physiological parameters of a subject using a sensor array. In an embodiment, a sensor array may contain sensor elements for determining multiple physiological parameters. A combination of sensor elements and the physiological parameters determined may be selected based on signals obtained from the sensor elements of the sensor array. A sensor array may be connected to a monitoring device that may select an optimal sensor element or combination of sensor elements and one or more physiological parameters to be determined. The monitoring device may then determine physiological parameters using the selected combination of sensor elements and display information associated with the parameters on a monitor for use, for example, in monitoring a medical patient.

10 Claims, 5 Drawing Sheets

(51) Int. Cl.
*A61B 5/024* (2006.01)
*A61B 5/08* (2006.01)

(56) References Cited

U.S. PATENT DOCUMENTS

| | | |
|---|---|---|
| 6,675,031 B1 | 1/2004 | Porges et al. |
| 7,006,856 B2 | 2/2006 | Baker et al. |
| 7,181,264 B2 | 2/2007 | Wiesmann et al. |
| 7,248,910 B2 | 7/2007 | Li et al. |
| 7,457,652 B2 | 11/2008 | Porges et al. |
| 7,751,340 B2 * | 7/2010 | Forbes et al. ............... 370/252 |
| 7,957,780 B2 * | 6/2011 | Lamego et al. ............... 600/322 |
| 8,133,176 B2 * | 3/2012 | Porges et al. ............... 600/300 |
| 2004/0097797 A1 | 5/2004 | Porges et al. |
| 2004/0138540 A1 * | 7/2004 | Baker et al. ............... 600/336 |
| 2006/0030764 A1 | 2/2006 | Porges et al. |
| 2006/0135860 A1 * | 6/2006 | Baker et al. ............... 600/310 |
| 2006/0258921 A1 | 11/2006 | Addison et al. |
| 2006/0270920 A1 | 11/2006 | Al-Ali et al. |
| 2008/0300471 A1 | 12/2008 | Al-Ali et al. |
| 2009/0326386 A1 | 12/2009 | Sethi et al. |
| 2011/0021892 A1 | 1/2011 | Addison et al. |

\* cited by examiner

SYSTEMS AND METHODS FOR PROVIDING SENSOR ARRAYS FOR DETECTING PHYSIOLOGICAL CHARACTERISTICS

CROSS REFERENCE TO RELATED APPLICATION

This application claims the benefit of U.S. Provisional Application No. 61/260,743, filed Nov. 12, 2009, which is hereby incorporated by reference in its entirety.

SUMMARY

The present disclosure is related to signal processing systems and methods, and more particularly, to systems and methods for detecting one or more physiological characteristics of a subject using a sensor array.

In an embodiment, a sensor array may include a plurality of sensor elements capable of detecting physiological characteristics of a subject. The sensor elements in the array may be of any suitable type and may detect any number of physiological characteristics. Groups of sensor elements in the array may detect the same or different physiological characteristics. Each individual sensor element may detect a single physiological characteristic, or individual sensor elements in the array may detect more than one physiological characteristic. Sensor elements in the array may communicate with other sensor elements in the array or with a monitoring device connected to the sensor array.

In an embodiment, measurements received from a sensor array may be analyzed to select a suitable measurement type to obtain using the sensor array. The selection may include comparing characteristics of signals received from the sensor array to a predefined set of metrics and thresholds. The selection may also be made based on the locations of different sensor arrays or different sensor elements in sensor arrays. The selection may be made based on the correlation between signals received from the sensor array and models for available measurement types. A set of available measurement types may be predefined, and the suitable measurement type may be selected from the set of available measurement types.

In an embodiment, combinations of sensor elements may be evaluated for selection of a best combination or combinations of sensor elements to use for determining one or more physiological parameters. The combinations may include sensor elements from one or more sensor arrays. The measurement type obtained from the combinations of sensors may be a predefined measurement type. The measurement types obtained from the combinations of sensor elements may also be determined after the best combinations of sensor elements are selected. All possible combinations of available sensor elements may be evaluated before a final best combination of sensor elements is selected. Alternatively, combinations of available sensor elements may be evaluated only until a first suitable combination of sensor elements is found, and that suitable combination of sensor elements may be used for monitoring.

In an embodiment, a sensor array may be coupled to a monitoring device that obtains measurements from the sensor array and performs selection of combinations of sensor elements and suitable measurement types used for monitoring. The monitoring device may be coupled to other sensor units in addition to a sensor array and may be coupled to more than one sensor array. The monitoring device may test combinations of sensor elements from just one sensor array to which it is attached, or may test combinations of sensor elements from any number of sensor arrays to which it is attached. The monitoring device may be coupled to a multi-parameter monitor that may display information associated with the physiological parameters being determined, the various measurement types being obtained, and/or the combinations of sensor elements being used to obtain measurements.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION

Figure 1A:
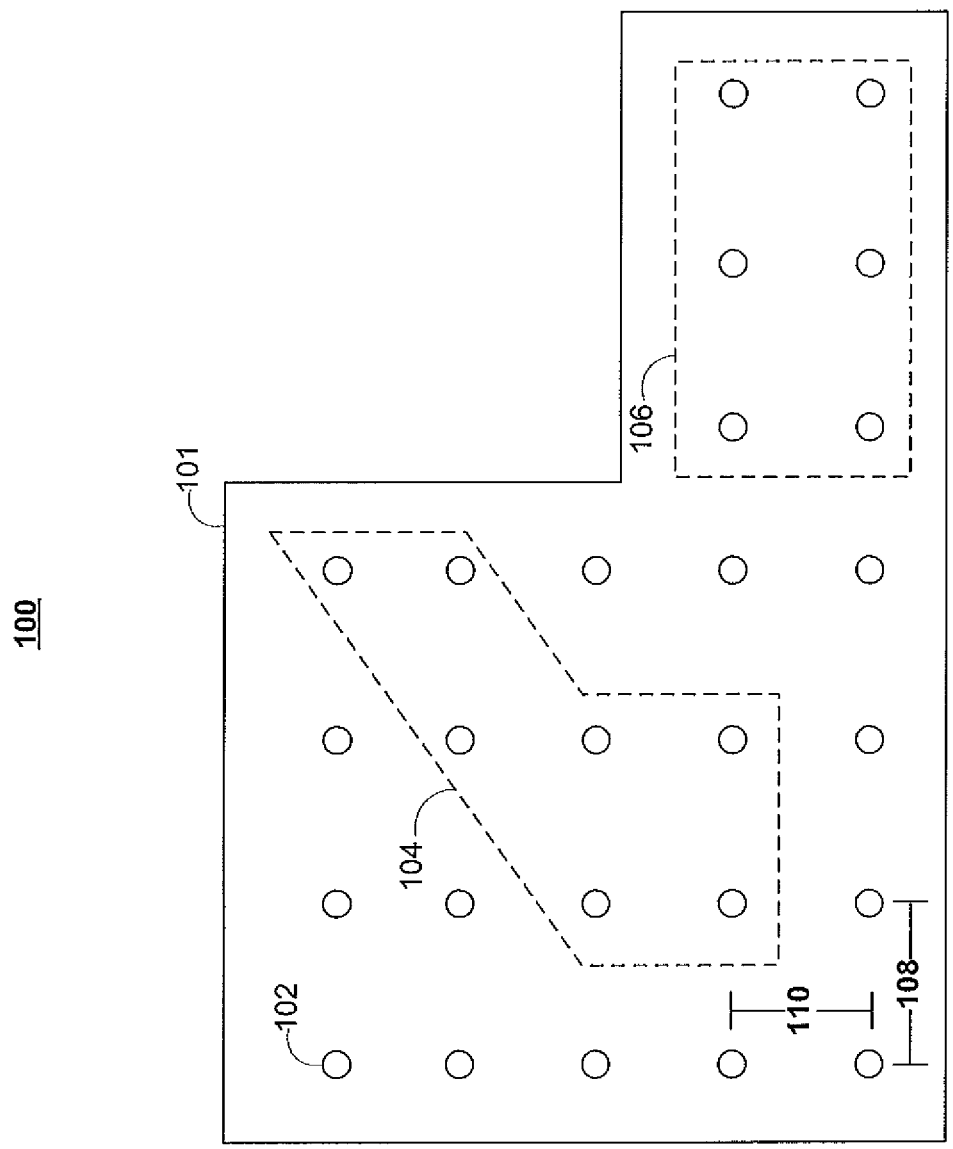
FIG. 1(a) depicts a block diagram of a sensor array according to an illustrative arrangement.

Monitoring the physiological state of a subject, for example, by determining, estimating, and/or tracking one or more physiological parameters of the subject, may be of interest in a wide variety of medical and non-medical applications. Knowledge of a subject's physiological characteristics (e.g., through a determination of one or more physiological parameters such as blood pressure, oxygen saturation, and presence of specific heart conditions) can provide short-term and long-term benefits to the subject, such as early detection and/or warning of potentially harmful conditions, diagnosis and treatment of illnesses, and/or guidance for preventative medicine.

One type of device that can be used to monitor the physiological state of a subject is an oximeter. An oximeter is a medical device that may determine, for example, the oxygen saturation of blood. An oximeter may include a light sensor that is placed at a site on a patient, typically a fingertip, toe, forehead or earlobe, or, in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured and other physiological parameters such as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less red light and more infrared light than blood with a lower oxygen saturation.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

In pulse oximetry, by comparing the intensities of two wavelengths at different points in the pulse cycle, it is possible to estimate the blood oxygen saturation of hemoglobin in arterial blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

For example, using a pulse oximeter, saturation may be calculated by solving for the "ratio of ratios" as follows.
1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A-log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{\frac{dI}{dt}}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2,\lambda_{IR}) - I(t_1,\lambda_{IR})]I(t_1,\lambda_R)$$

$$y(t) = [I(t_2,\lambda_R) - I(t_1,\lambda_R)]I(t_1,\lambda_{IR}) \quad (8)$$

$$y(t) = Rx(t)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

The foregoing is merely illustrative and any suitable processing techniques may be used to calculate pulse oximetry values. For example, Fourier transforms and continuous wavelet transforms may be used to process the PPG signals and derive blood oxygen saturation.

In regional oximetry, by comparing the intensities of two wavelengths of light, it is possible to estimate the blood oxygen saturation of hemoglobin in a region of a body. Whereas pulse oximetry measures blood oxygen based on changes in the volume of blood due to pulsing tissue (e.g., arteries), regional oximetry may examine blood oxygen saturation within the venous, arterial, and capillary systems within a region of a patient. A regional oximeter is another common type of oximeter, which may be used to calculate an oxygen saturation of a patient's blood in a non-invasive manner. For example, a regional oximeter may include a sensor to be placed on a patient's forehead and may be used to calculate the oxygen saturation of a patient's blood within the venous, arterial and capillary systems of a region underlying the patient's forehead (e.g., in the cerebral cortex). The sensor may include two emitters and two detectors: one detector that is relatively "close" to the two emitters and another detector that is relatively "far" from the two emitters.

For example, if $I_A$ represents the intensity of the received/detected light associated with the "close" detector, $$\frac{I_A(\lambda, t)}{I_O(\lambda)},$$

may be derived using Lambert-Beer's law, described above. Similarly, if $I_B$ represents the intensity of the received/detected light associated with the "far" detector, $$\frac{I_B(\lambda, t)}{I_O(\lambda)},$$

may be derived using Lambert-Beer's law, described above. Light intensity of multiple wavelengths may be received at both the "close" and the "far" detectors. For example, if two wavelength were used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Other methods to calculate regional blood oxygen saturation are well known in the art.

PPG sensors may also be affixed to a subject and allow for the determination of the subject's blood pressure, for example, using continuous non-invasive blood pressure (CNIBP) techniques. For example, some continuous non-invasive blood pressure monitoring techniques have been developed that involve the use of two probes or sensors positioned at two different locations on a subject's body. The elapsed time, T, between the arrival of corresponding points of a pulse signal at the two locations may then be determined using the two probes or sensors. The estimated blood pressure, p, may then be related to the elapsed time, T, by $$p = a + b \cdot \ln(T) \tag{9}$$

where a and b are constants that are dependent upon the nature of the subject and the signal detecting devices. Other blood pressure equations using elapsed time may also be used.

Such a continuous and non-invasive blood pressure monitoring technique is described in Chen et al. U.S. Pat. No. 6,599,251, which is hereby incorporated by reference herein in its entirety. The technique described by Chen et al. may use two sensors (e.g., ultrasound or photoelectric pulse wave sensors) positioned at any two locations on a subject's body where pulse signals are readily detected. For example, sensors may be positioned on an earlobe and a finger, an earlobe and a toe, or a finger and a toe of a patient's body. In some approaches, a single sensor or probe location may be used to determine blood pressure, as described in U.S. patent publication No. 2009/0326386, published Dec. 31, 2009, which is hereby incorporated by reference herein in its entirety.

Similar sensors or probes may also be used to determine respiration rate and other respiratory properties (e.g., respiratory effort). For example, as described in more detail in U.S. Patent App. Pub. No. 2006/0258921, which is incorporated by reference herein in its entirety, the act of breathing may cause a breathing band to become present in a scalogram derived from a continuous wavelet transform of a PPG signal. This breathing band may occur at or about the scale having a characteristic frequency that corresponds to the breathing frequency. Furthermore, the features within this band (e.g., the energy, amplitude, phase, or modulation) or the features within other bands of the scalogram may result from changes in breathing rate (or breathing effort) and therefore may be correlated with various respiratory parameters of a patient.

As is well known in the art, sensors may also be used to determine other physiological characteristics of a subject. For example, an electrical physiological signal (EPS) sensor may be used to determine such signals as electroencephalographic (EEG) signals, electrocardiography (ECG or EKG) signals, electromyography (EMG) signals, or any other electrical physiological signal. Sensors may also be used to determine a subject's body temperature, a pulse transit times (PTT), or both. In some embodiments, PTT may be determined by using plethysmograph data in conjunction with ECG data. For example, PTT may be determined by comparing an ECG onset point with a PPG arrival point. An ECG signal may be processed in order to detect the QRS complex and to detect the R wave peak. The plethysmograph signal may be processed to detect the pulse timing. The PTT may then be calculated as the time between the R wave peak and the corresponding pulse peak. Other suitable techniques for calculating PTT are well know in the art and may also be used. Any of the aforementioned physiological characteristics may be determined using the sensor array of the present disclosure.

FIG. 1(a) shows illustrative sensor array 100. Sensor array 100 may include a plurality of sensor elements 102, which may be of the same or different types. Sensor array 100 may also include processing circuitry (e.g., one or more microprocessors), memory (e.g., RAM, ROM, and hybrid types of memory), storage (e.g., one or more hard drives, tape drives, or optical drives), and a communications interface (e.g., a wireless network controller, serial port, or infrared port). Sensor array 100 may be configured to be placed over a local area of a subject's body. Sensor array 100 may include a plurality of sensors elements 102 connected by flexible sheet 101. Flexible sheet 101 may include any mesh, netting, fabric, plastic, other suitable polymer, or any combination of the foregoing. In some embodiments, flexible sheet 101 may be configured to be worn by a patient, for example, as an article of clothing. For example, flexible sheet 101 may be incorporated into a glove, hat, armband, headband, wristband, back strap, chest strap, or any other suitable article. One or more of sensors elements 102 of sensor array 100 may be, for example, an electrode, a complementary metal oxide semiconductor (CMOS) sensor, a charged coupled device (CCD) sensor, or a combination CMOS/CCD sensor. The CCD sensor may comprise a photoactive region and a transmission region for receiving and transmitting data whereas the CMOS sensor may be made up of an integrated circuit having an array of pixel sensors. Each pixel may have a photodetector and an active amplifier. One or more of sensor elements 102 may also be a flexible probe as described in U.S. patent application Ser. No. 12/508,180, filed Jul. 23, 2009, which is hereby incorporated by reference herein in its entirety. In an embodiment, sensor elements 102 in sensor array 100 may be configured to emit a single wavelength of light. For example, a first sensor element may emit only a RED light while a second may emit only an IR light. In an embodiment, sensor elements 102 in sensor array 100 may be configured to emit more than one wavelength (e.g., RED and IR light).

Each sensor element 102 of sensor array 100 may include one or more of an emitter portion and a detector portion. The detector portion may be configured to detect the intensity of light at particular wavelengths, such as the RED and IR wavelengths. Alternatively, one or more sensor elements 102 in sensor array 100 may be configured to detect an intensity of a single wavelength. In operation, light may enter a detector portion after passing through the subject's tissue. The detector portion may convert the intensity of the received light into an electrical signal. The light intensity may be directly related to the absorbance and/or reflectance of light in the subject's tissue. That is, when more light at a certain wavelength is absorbed or reflected by the tissue, less light of that wavelength may be received from the tissue by the detector portion. After converting the received light to an electrical signal, the detector portion may send the signal to a monitor (not shown), where physiological characteristics or parameters may be calculated based on the absorption of the RED and IR wavelengths in the subject's tissue. In an embodiment, some or all of the calculations may be performed by sensor array 100 itself, and the result of the calculations may be passed to a monitor. Each sensor element 102 in sensor array 100 (or a combination of sensor elements) may take the form of a local oxygen saturation sensor, a regional oxygen saturation sensor, a respiration rate sensor, a respiratory effort sensor, a blood pressure sensor, a temperature sensor, an EPS sensor, any other type of physiological measurement sensor, or any combination of the foregoing types of sensors.

In an embodiment, sensor elements 102 or sensor array 100 may be connected to and draw its power from a monitor (not shown). In another embodiment, sensor elements 102 or sensor array 100 may be wirelessly connected to the monitor and include its own battery or similar power supply (not shown). The monitor may be configured to calculate physiological parameters based at least in part on data received from the sensor elements 102 in sensor array 100.

Although in the example of FIG. 1(a), twenty-six sensor elements are included in sensor array 100, sensor array 100 may include any number of sensor elements. The sensor elements may be arranged in a grid layout, a rectangular layout, or a layout of any suitable geometry. For example, sensor array 100 may be incorporated with flexible sheet 101 and take a circular, square, rectangular, hexagonal, irregular, or free-form shape. Each sensor element 102 may be separated from the next sensor element 102 in the same row by width 108 and separated from the next sensor element 102 in the same column by height 110. Width 108 and height 110 may be the same distance or different distances. In addition, width 108 and height 110 may remain constant throughout sensor array 100 or may vary from one portion of the array to the next. Other suitable geometries and layouts for sensor array 100 and flexible sheet 101 may also be used.

One or more sensors may be grouped or combined into a sensor element region, such as sensor element regions 104 and 106. Sensor element regions may include any number of sensors of the same or different type used for determining the same or different physiological parameters. For example, some locations on a subject's body may be better suited to detect blood pressure, while other locations on a subject's body may be better suited to detect oxygen saturation. In an embodiment, sensor elements in a region corresponding to a location on a subject's body that is more suited for detecting a particular type of physiological parameter (e.g., blood pressure, pulse rate, or oxygen saturation) may include sensor elements operative to detect that type of parameter. In an embodiment, a single sensor element 102 may be capable of being used to determine more than one physiological parameter. For example, as described below in connection with FIGS. 2 and 3, sensor element 102 may detect one or more physiological signals and may be used to determine whatever physiological parameter or parameters that have the greatest signal quality or signal strength at that particular location. In this way, one or more of sensor elements 102 may be generic sensors capable of being used to determine multiple physiological parameters of different types.

Each sensor element 102 in sensor array 100 may communicate with other sensor elements via the monitor. Individual sensor elements may communicate directly or may communicate indirectly, for example, through a monitor connected to sensor array 100. In some embodiments, sensor elements may communicate with the monitor wirelessly (e.g., using RFID or any other wireless network protocol). In an embodiment, sensor elements may also communicate with other sensor elements in the same sensor element region in order to coordinate measurement types, exchange measurement data, and determine the optimal site and/or best sensor element combination for a measurement as described in more detail below.

Figure 1B:
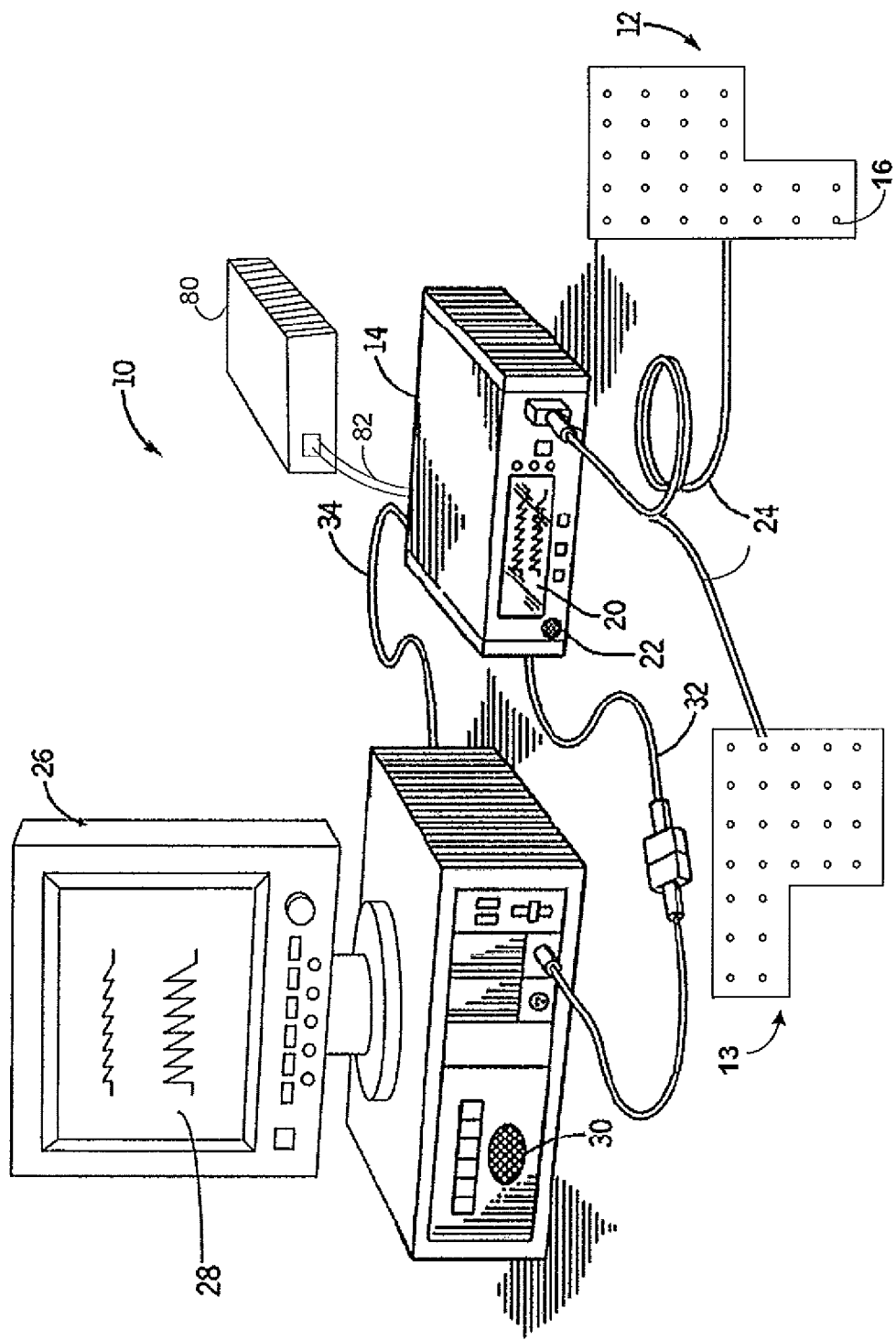
FIG. 1(b) shows a patient monitoring system according to an illustrative arrangement.

FIG. 1(b) is a perspective view of an embodiment of a patient monitoring system 10. System 10 may include sensor array 12 and monitor 14. Sensor array 12 may correspond to sensor array 100 (FIG. 1(a)). Sensor array 12 may include a plurality of sensor elements 16, which may be of the same or different types. Each sensor element 16 of sensor array 12 (or a combination of sensor elements) may take the form of a local oxygen saturation sensor, a regional oxygen saturation sensor, a respiration rate sensor, a respiratory effort sensor, a blood pressure sensor, a temperature sensor, an EPS sensor, any other type of physiological measurement sensor, or any combination of the foregoing types of sensor. Sensor elements 16 of sensor array 12 may include one or more emitters for emitting light at one or more wavelengths into a patient's tissue. Sensor elements 16 of sensor array 12 may also include one or more detectors for detecting the light produced by one or more emitters that emanates from the patient's tissue after passing through the tissue. Any suitable physical configuration of emitters and detectors may be used. According to an embodiment, emitters and detectors of sensor array 12 may be located on opposite sides of a digit such as a finger or toe, in which case the light that is emanating from the tissue has passed completely through the digit. In an embodiment, emitters and detectors of sensor array 12 may be arranged so that light from the emitters penetrates the tissue and is reflected by the tissue into the detectors, for example, to obtain oximetry data from a patient's forehead.

In an embodiment, system 10 may include one or more additional sensor units. Sensor units used in addition to sensor array 12 may include single-parameter or multi-parameter sensors or probes, such as the physiological sensors discussed above with respect to sensor elements 16. Sensor units used in addition to sensor array 12 may also include one or more sensor arrays, such as sensor array 13, which may correspond to sensor array 100 (FIG. 1(a)). Sensor array 13 may take the form of any of the embodiments described herein with reference to sensor array 12. Sensor array 13 may be the same type of sensor array as sensor array 12, or sensor array 13 may be of a different sensor array type than sensor array 12. Sensor arrays 12 and 13 may be capable of being positioned at two different locations on a subject's body; for example, sensor array 12 may be positioned on a patient's forehead, while sensor array 13 may be positioned at a patient's fingertip. In an embodiment, oxygen saturation measurements may be taken from both sensor array 12 positioned on a patient's forehead and sensor array 13 positioned at a patient's fingertip. The measurements obtained may be analyzed by monitor 14 to determine which sensor array location produces more reliable measurements based on signal integrity, confidence values, or any other suitable criteria. One of sensor array 12 and sensor array 13 may then be selected for continuous patient monitoring. In an embodiment, a combination of sensor elements from both sensor array 12 and sensor array 13 may be chosen for patient monitoring. The selection of sensor array elements for a certain measurement type will be described in more detail with respect to FIG. 3. One or more signals from one or more sensor elements and/or sensor arrays may be used in the measurement techniques described herein.

Sensor arrays 12 and 13 may each detect any signals that carry information about a patient's physiological state, such as an electrocardiograph signal, arterial line measurements, or the pulsatile force exerted on the walls of an artery using, for example, oscillometric methods with a piezoelectric transducer. It will be understood that any type of sensor element, including any type of physiological sensor element, may be used in one or more of sensor arrays 12 and 13 in accordance with the systems and techniques disclosed herein. It is understood that any number of sensor arrays measuring any number of physiological signals may be used to assess patient status in accordance with the techniques described herein.

In an embodiment, sensor arrays 12 and 13 may be communicatively coupled to monitor 14 via a cable 24. Sensor arrays 12 and 13 may draw power from monitor 14 through cable 24. In an embodiment, a wireless transmission device (not shown) or the like may be used instead of or in addition to cable 24, and sensor arrays 12 and 13 may include their own battery or similar power supply (not shown). Monitor 14 may be configured to determine physiological parameters (e.g., heart rate, blood pressure, blood oxygen saturation) based at least in part on data received from one or more sensor units, such as sensor arrays 12 and 13, relating to light emission and detection. In an embodiment, the sensor unit itself may determine the physiological parameters, and the parameters may be passed to monitor 14. Further, monitor 14 may include a display 20 configured to display the physiological parameters or other information about the system. In the embodiment shown, monitor 14 may also include a speaker 22 to provide an audible sound that may be used for various other embodiments, such as for example, sounding an audible alarm if a patient's physiological parameters are not within predefined normal ranges.

In the illustrated embodiment, system 10 may also include a multi-parameter patient monitor 26. The multi-parameter patient monitor 26 may include a cathode ray tube display, a flat panel display (as shown) such as a liquid crystal display (LCD) or a plasma display, or may include any other type of monitor now known or later developed. Multi-parameter patient monitor 26 may be configured to determine physiological parameters and to provide a display 28 for information from monitor 14 and from other medical monitoring devices or systems (not shown). For example, multi-parameter patient monitor 26 may be configured to display an estimate of a patient's blood oxygen saturation generated by monitor 14 (referred to as an "SpO$_2$" measurement), pulse rate information from monitor 14, and blood pressure measurement from monitor 14 on display 28. In an embodiment, multi-parameter patient monitor 26 may display information associated with different types of measurements received from sensor arrays 12 and 13. In an embodiment, the information may include information used to choose a certain measurement type to be obtained by sensor arrays 12 and 13. In an embodiment, multi-parameter patient monitor 26 may display information identifying the combination of sensor elements being used to obtain certain measurements. The combinations and measurement types may be chosen, for example, by the processes described below with respect to FIGS. 2 and 3. Monitor 26 may include a speaker 30 that may be used to sound audible alarms based on data received from monitor 14.

Monitor 14 may be communicatively coupled to multi-parameter patient monitor 26 via a cable 32 or 34 that is connected to a sensor input port or a digital communications port, respectively, and/or may communicate wirelessly (not shown). In addition, monitor 14 and/or multi-parameter patient monitor 26 may be coupled to a network to enable the sharing of information with servers or other workstations (not shown). Monitor 14 may be powered by a battery or by a conventional power source such as a wall outlet.

Calibration device 80, which may be powered by monitor 14 via a cable 82, a battery, or by a conventional power source such as a wall outlet, may include any suitable signal calibration device. Calibration device 80 may be communicatively coupled to monitor 14 via cable 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Calibration device 80 may also access reference signal measurements stored in memory (e.g., RAM, ROM, or a storage device). For example, in some embodiments, calibration device 80 may access reference blood pressure measurements from a relational database stored within calibration device 80, monitor 14, or multi-parameter patient monitor 26. The reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. Reference blood pressure measurement may be generated when recalibration is triggered.

Figure 1C:
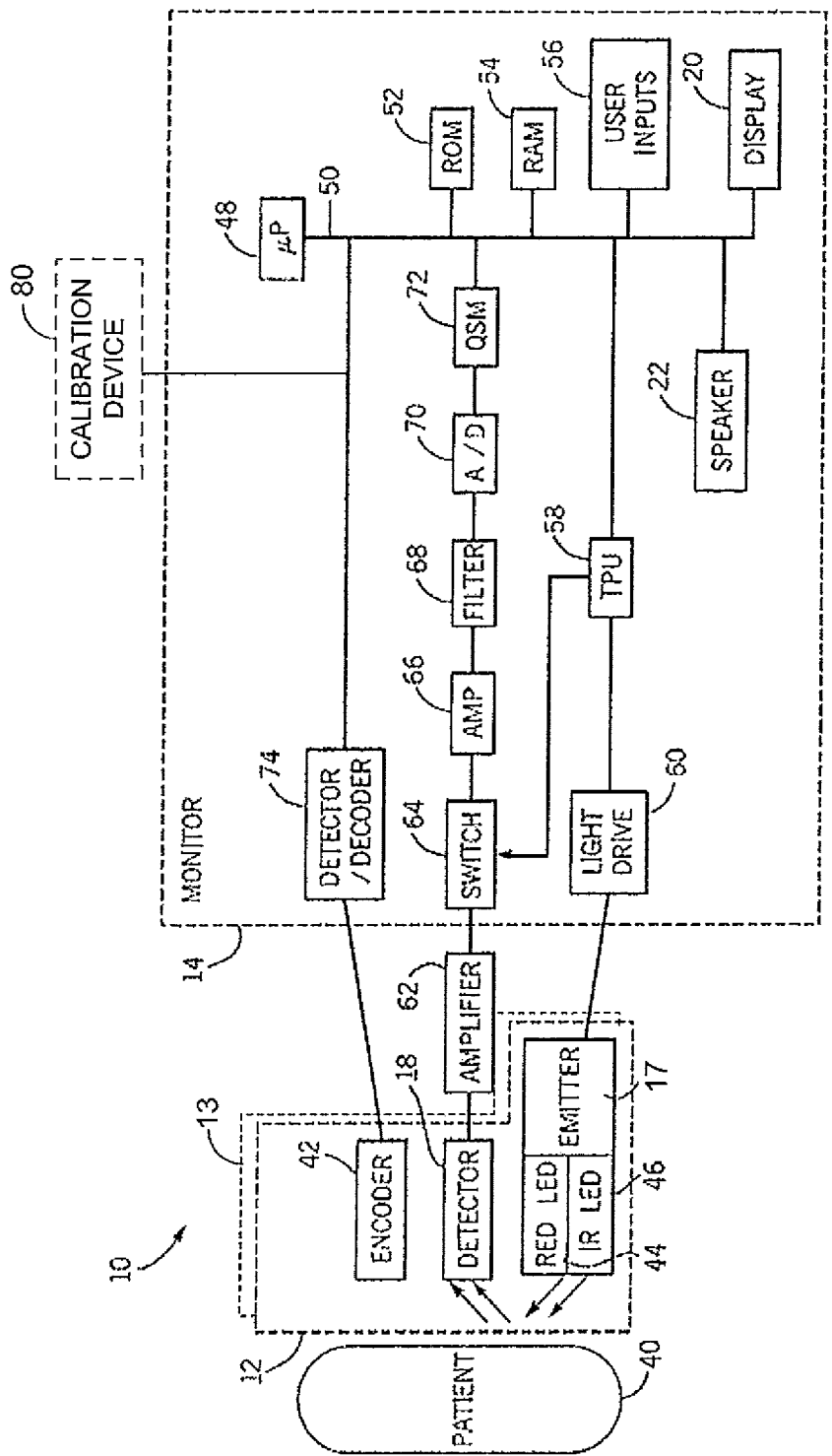
FIG. 1(c) is a block diagram of the patient monitoring system of FIG. 1(b) coupled to a patient according to an illustrative arrangement.

FIG. 1(c) is a block diagram of a patient monitoring system, such as patient monitoring system 10 of FIG. 1(b), which may be coupled to a patient 40 in accordance with an embodiment. Certain illustrative components of sensor array 12 and monitor 14 (FIG. 1(b)) are shown in FIG. 1(c). Sensor arrays 12 and 13 may include similar functionality, and it will be understood that any of the concepts, components, features, and operations discussed in connection with sensor array 12 may be applied to sensor array 13 as well (e.g., emitter portion 17 and detector portion 18 of sensor array 12 may be similar to emitter and detector portions of sensor array 13). It will be noted that patient monitoring system 10 may include one or more additional sensor arrays or probes, which may take the form of any of the embodiments described herein with reference to sensor arrays 12 and 13 (FIG. 1(b)), or any other suitable sensor units. For the purpose of illustration and not limitation, one emitter portion and one detector portion are shown in sensor array 12, but any number or type of sensor elements may be included in sensor array 12. Additional sensor elements in sensor array 12 may include additional emitters and detectors, blood pressure sensors, temperature sensors, EPS sensors, any other type of physiological measurement sensor, or any combination of the foregoing types of sensors. In an embodiment, multiple sensor elements (distributed in one or more sensor arrays) may be located at multiple different body sites on a patient.

The sensor elements in sensor array 12 may include an emitter portion 17, a detector portion 18, and an encoder 42. Emitter portion 17 and detector portion 18 may each include one or more sensor elements 16 (FIG. 1(b)). In the embodiment shown, emitter portion 17 may be configured to emit at least two wavelengths of light (e.g., RED and IR) into a patient's tissue 40. Hence, emitter portion 17 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. Individual sensor elements 16 (FIG. 1(b)) within emitter portion 17 may each be configured to emit a single wavelength. For example, a first sensor element emits only a RED light while a second sensor element only emits an IR light. In another example, the wavelengths of light used are selected based on the specific location of the sensor.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector portion 18 may be selected to be specifically sensitive to the chosen targeted energy spectrum of the emitter portion 17.

In an embodiment, an individual sensor element may be configured to detect the intensity of light at both the RED and IR wavelengths. Alternatively, individual sensor elements in the array may each be configured to detect an intensity of a single wavelength. In operation, light may enter detector portion 18 after passing through the patient's tissue 40. Detector portion 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector portion 18. After converting the received light to an electrical signal, detector portion 18 may send the signal to monitor 14, where physiological parameters may be calculated based on the absorption of the RED and IR wavelengths in the patient's tissue 40. Monitor 14 may also determine physiological parameters based on signals received from sensor elements of sensor array 12 that are not included in emitter portion 17 or detector portion 18. Monitor 14 may determine any physiological parameter based on signals received from sensor elements, including oxygen saturation, blood pressure, pulse rate, respiratory rate, heart rate, any other suitable physiological characteristic, or any combination of suitable physiological characteristics. Each physiological parameter may be determined based on signals received from a single sensor element or a combination of sensor elements.

In an embodiment, encoder 42 may contain information about sensor array 12, such as what type of sensor array it is (e.g., whether the sensor array is intended for placement on a forehead or digit), the different sensor elements contained in the sensor array, and/or the wavelengths of light emitted by emitter portion 17. This information may be used by monitor 14 or calibration device 80 to select appropriate algorithms, lookup tables and/or calibration coefficients stored in monitor 14 or calibration device 80 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which, for example, oxygen saturation, pulse rate, blood pressure, and other measurements may be determined based at least in part on the signal or signals received at sensor array 12. For example, some oximetry sensors rely on equations to relate an area under a pulse of a photoplethysmograph (PPG) signal to determine blood pressure. These equations may contain coefficients that depend upon a patient's physiological characteristics as stored in encoder 42. The information stored in encoder 42 may be used in retrieving a set of coefficients from calibration device 80 to be used for calculations. Encoder 42 may, for instance, be a coded resistor which stores values corresponding to the type of sensor array 12 or the type of each sensor element in sensor array 12, the wavelengths of light emitted by emitter portion 17, and/or the patient's characteristics. In an embodiment, encoder 42 may include a memory on which one or more of the following information may be stored for communication to monitor 14: the type of the sensor array 12, the different types of sensor elements in sensor array 12, the wavelengths of light emitted by emitter portion 17, the particular wavelength each sensor element in sensor array 12 is monitoring, a signal threshold for each sensor element in sensor array 12, any other suitable information, or any combination thereof.

In an embodiment, signals from detector portion 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by Microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitters in emitter portion 17 are illuminated and multiplexed timing for the RED LED 44 and the JR LED 46. TPU 58 may also control the gating-in of signals from detector portion 18 through an amplifier 62 and a switching circuit 64. These signals are sampled at the proper time, depending upon which light sources are illuminated. The received signals from detector portion 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received. TPU 58 may also control the timing and operation of additional sensor elements in sensory array 12 that are not depicted in FIG. 1(c).

In an embodiment, microprocessor 48 may determine the patient's physiological parameters, such as $SpO_2$, blood pressure, pulse rate, respiratory rate, heart rate, any other suitable physiological parameter, or any combination of suitable physiological parameters, using various algorithms and/or look-up tables based on the values of the received signals and/or data corresponding to the light received by detector portion 18 or signals received from other sensor elements of sensor array 12. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based at least in part on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

In an embodiment, microprocessor 48 may analyze data received from sensor array 12 to determine a certain measurement type (e.g., a certain physiological parameter) to obtain from sensor array 12. In an embodiment, microprocessor 48 may analyze data received from different combinations of sensor elements from one or more sensor arrays to identify an optimal sensor element or combination of sensor elements to obtain a certain measurement type (e.g., a certain physiological parameter).

Figure 2:
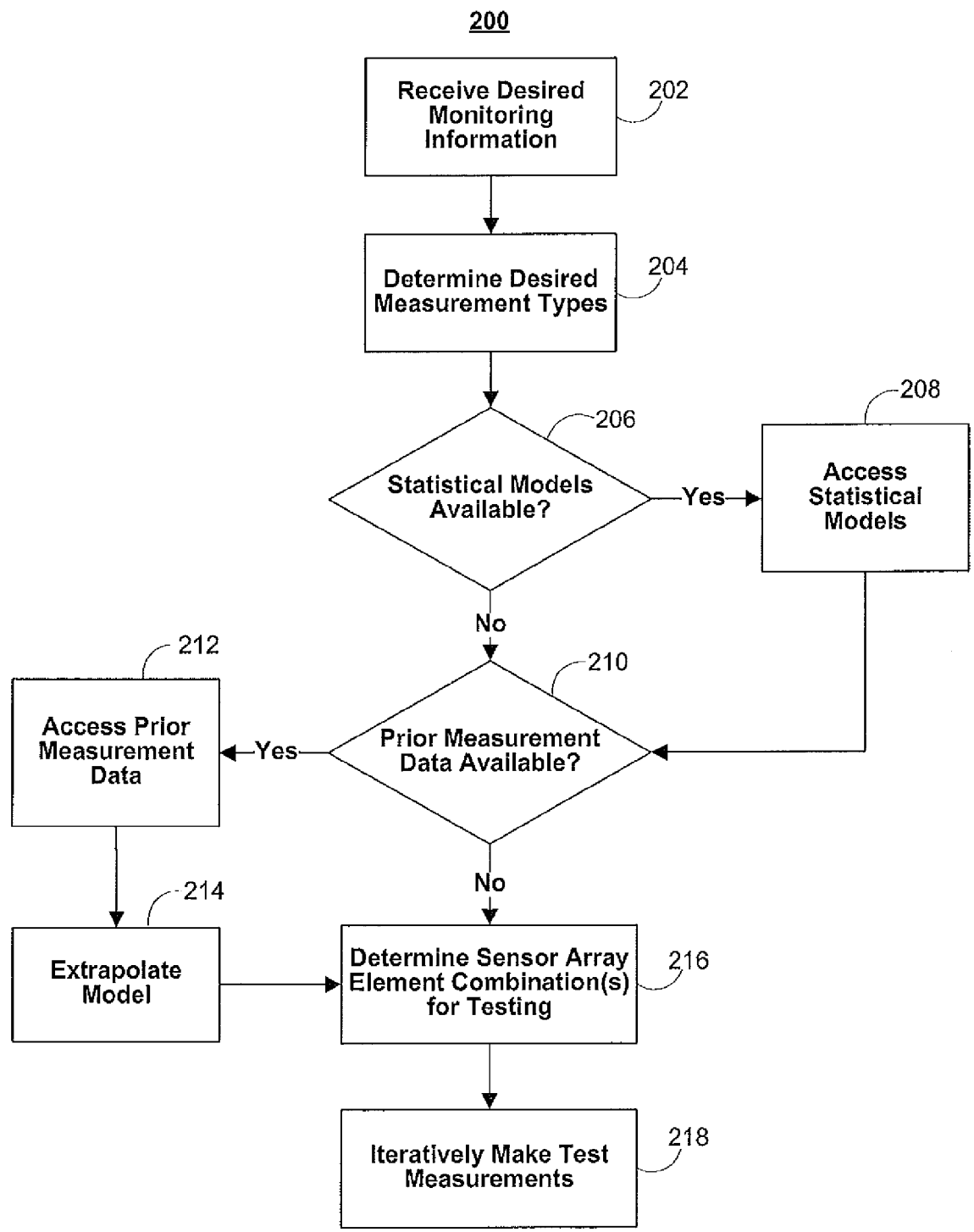
FIG. 2 is a flowchart depicting an illustrative process for using a sensor array to take at least one physiological characteristic measurement according to an illustrative arrangement.

FIG. 2 shows illustrative process 200 for using a sensor array to take at least one physiological measurement. Some locations on a subject's body may yield better measurements for certain measurement types than other locations on the subject's body. By using an array, such as sensor array 100 (FIG. 1(a)), a medical practitioner can apply the array to a general location on a subject's body (e.g., the forehead, wrist, arm, back, head, or hand), and an optimal combination of sensor elements in the array may be selected for use in determining a particular measurement.

At step 202, desired monitoring information may be received. The desired monitoring information may include, for example, a test specification identifying variables for testing. For example, healthcare personnel may input a test specification into a monitoring device (e.g., monitor 14 (FIG. 1(b))) connected to a sensor array (e.g., sensor array 100 (FIG. 1(a))). The test specification may indicate which types of measurements to take (e.g., oxygen saturation, blood pressure, and/or pulse rate), the measurement frequency (for continuous measurement, for example, every five seconds), an absolute time a measurement is needed (for single measurements, for example, within 60 seconds), a desired signal integrity or confidence value, or any other suitable information.

At step 204, the desired measurement types may be determined from the received desired monitoring information. For example, the monitoring information may indicate that measurements for local oxygen saturation, regional oxygen saturation, blood pressure, PTT, one or more EPS, respiration rate, respiratory effort, temperature, and pulse rate may be desired. At step 206, sensor array 100 (FIG. 1(a)) or the monitor connected to sensor array 100 (e.g., monitor 14 (FIG. 1(b))) may determine if one or more statistical models are available for the desired measurement type or types. If such models are available, they may be accessed at step 208. For example, in an embodiment, a data modeling processor included with sensor array 100 (FIG. 1(a)) or the monitor connected to sensor array 100 (e.g., monitor 14 (FIG. 1(b))) may include a linear or non-linear statistical data modeling module that identifies valid signal segments for a particular measurement type. The modeling processor (which may take the form of an artificial neural network (ANN) in some embodiments) may be trained to identify signal segments that are valid for use in determining physiological parameters. For example, in some embodiments, the data modeling processor may perform one or more regression analyses (e.g., using linear or nonlinear regression techniques) on the input data. Valid signal segments may then be identified and may include segments identified as not having artifact (or having less than some threshold level of artifact), segments that are not stale (e.g., segments collected within some user-defined freshness time threshold), segments with a suitable signal-to-noise ratio, segments with a suitable signal quality, segments with any other suitable characteristics, or segments with any combination of the foregoing characteristics.

The data modeling processor may operate directly on the detected signal itself (e.g., a PPG signal) or some transform of the detected signal (e.g., a continuous wavelet transform of a PPG signal). In some embodiments, the data modeling processor may also operate on a scalogram derived from the transformed signal, a wavelet ratio surface, the real part of the wavelet transform, the imaginary part of the wavelet transform, the modulus of the wavelet transform, the energy density of the wavelet transform, or any combination of the foregoing signals. For example, the data modeling processor may recognize the pulse band in a scalogram derived from a continuous wavelet transform of a PPG signal prior to corruption by artifact. The data modeling processor may then detect an unrecognizable (or low fidelity) pulse band during artifact corruption.

In an embodiment, the data modeling processor may learn signal characteristics associated with a particular physiological parameter to be determined using a supervised learning phase. In an embodiment, the data modeling processor may implement a self-organizing map (SOM) feature (e.g., using a Kohonen map) that is trained using an unsupervised learning phase. A reinforcement learning phase (e.g., one that discovers a policy that minimizes some long-term cost metric) may additionally or alternatively be employed.

The statistical models accessed at step 208 may additionally or alternatively include an indication of one or more metrics defining signals suitable for use in determining a particular type of measurement. For example, signal quality and signal strength may be two useful metrics. The statistical models may include threshold values for one or more of these metrics. Measurements may be indicated as valid only when threshold values for all available metrics are met. For example, to determine respiration rate, a breathing band may be identified in a scalogram of a detected signal. Depending on the location of the sensor (e.g., sensor element 102 of FIG. 1(a)) in the array (e.g., sensor array 100 of FIG. 1(a)), signals of varying qualities may be detected. For example, artifact or other types of noise may corrupt, distort, or make the breathing band difficult to identify in the scalogram. Thus, signal quality may be lower at some locations than at other locations. As another example, the pulse band may be identified in order to determine the subject's pulse rate. If a strong pulse band is detected by the data modeling processor, this signal may be associated with a high signal strength whereas signals with weak pulse bands may be associated with lower signal strengths.

If no statistical models are available at step 206 or after accessing the statistical models at step 208, process 200 continues to determine if prior valid measurement data is available at step 210. If prior data is available, then that data may be accessed at step 212. The prior measurement data may represent previously-known good data and be used to extrapolate a statistical model at step 214, using, for example, a linear or nonlinear regression analysis or other statistical pattern recognition or modeling techniques. After a model has been extrapolated at step 214 or if no prior measurement data is available at step 210, a sensor array element combination may be determined for testing at step 216. For example, a series of contiguous or non-contiguous sensor elements (e.g., sensor elements 102 of FIG. 1(a)) in a sensor region (e.g., sensor regions 104 or 106 of FIG. 1(a)) may represent one element combination. In an embodiment, all possible element combinations in sensor array 100 (FIG. 1(a)) may be tested for each measurement type to yield the preferred measurement, as described in more detail in connection with FIG. 3. In an embodiment, arbitrary combinations may be tested until a suitable measurement (e.g., meeting the modeling metric thresholds) is discovered. In an embodiment, combinations of sensor elements from more than one sensor array (e.g., sensor arrays 12 and 13 (FIG. 1(b)) may be tested as a single combination.

In some embodiments, location data is accessed at step 216 in order to determine sensor array element combinations for testing. For example, based on historical or empirical data, a location corresponding to a particular area of a subject's temple may be a more suitable location for determining blood pressure while a different area of the subject's temple may be more suitable for determining oxygen saturation. If location data is available about the current sensor array (e.g., the array's positioning on the subject's body), this data may be used to determine appropriate element combinations for testing (e.g., depending on the measurement type or types desired).

At step 218, test measurements may be iteratively made at the sensor array element combinations selected at step 216. For example, test measurements may be made serially, one after another, or multiple measurements may be made simultaneously using different combinations of sensor array elements. The measurements made at step 218 may be used for continuous patient monitoring for the desired physiological characteristic, or the measurements may also be used to select a measurement type to obtain from the selected sensor array combination, for example, by the process discussed below with respect to FIG. 3.

Figure 3:
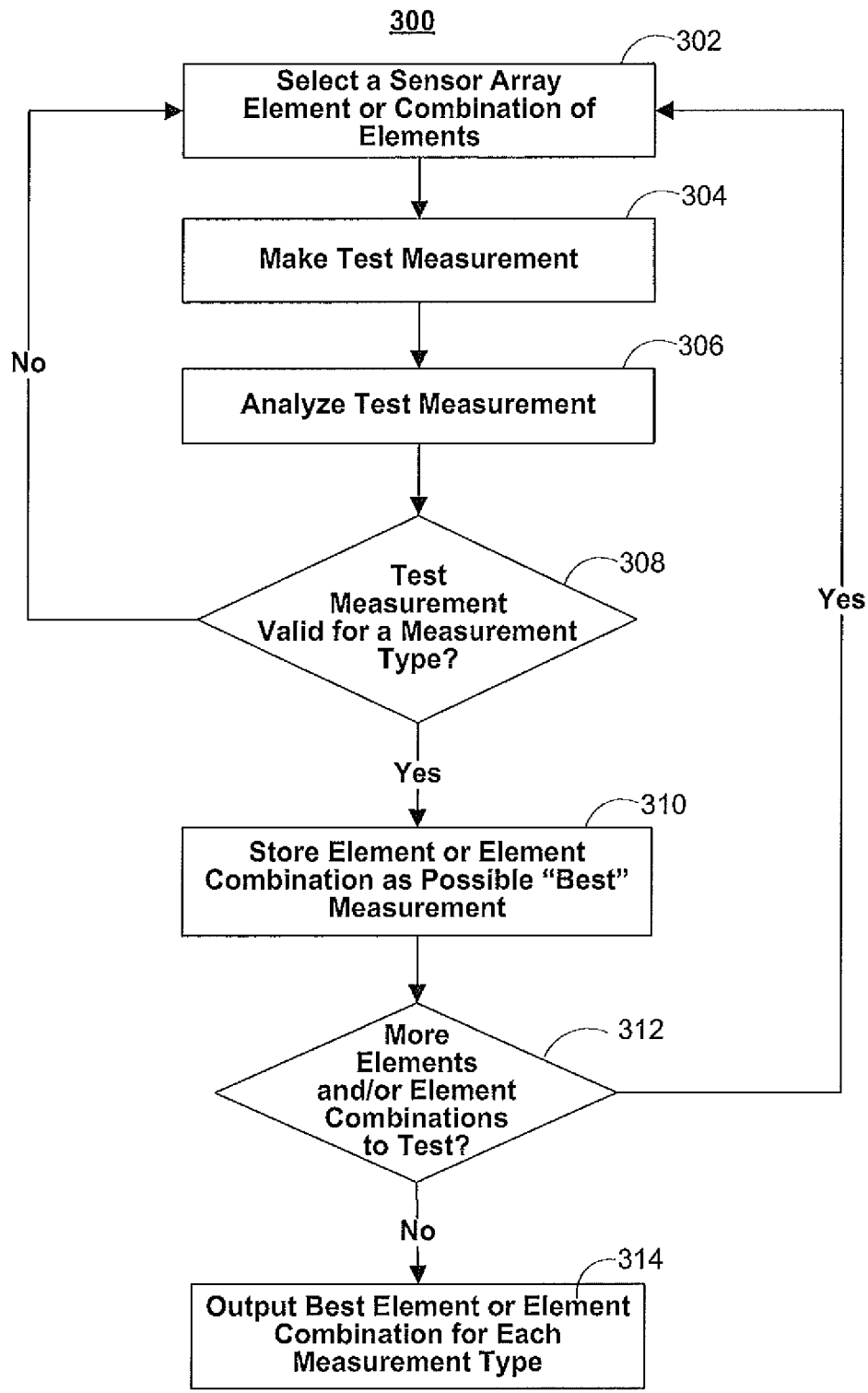
FIG. 3 is a flowchart depicting an illustrative process for determining which physiological measurements can be detected using a sensor array according to an illustrative arrangement.

FIG. 3 is a flowchart depicting an illustrative process 300 for determining which physiological measurements can be detected using a sensor array. Sometimes, it is desirable to combine multiple sensors into a single sensor in order to minimize the number of sensors (and leads) connected to a subject. By combining multiple sensor elements into an array, such as sensor array 100 (FIG. 1(a)), measurements for multiple different measurement types may be taken with a single application of the array. In addition, the sensor array may be applied to different parts of a body from which different physiological measurements can be detected.

At step 302, a sensor array element or element combination is selected. Sensor array elements may be selected from one or more sensor arrays (e.g., sensor arrays 12 and 13 (FIG. 1(b)) for a single combination. At step 304, a test measurement may be taken using the selected sensor array element or element combination. For example, some or all of the sensor elements in sensor region 104 (FIG. 1(a)) of sensor array 100 (FIG. 1(a)) may be used to obtain a PPG signal. The test measurement may then be analyzed at step 306. For example, sensor array 100 (FIG. 1(a)) or the monitor connected to sensor array 100 (e.g., monitor 14 (FIG. 1(b))) may compare the test measurement to one or more models. The models may indicate a valid signal for use in determining a physiological characteristic or combination of physiological characteristics.

At step 308, sensor array 100 (FIG. 1(a)) or the monitor connected to sensor array 100 (e.g., monitor 14 (FIG. 1(b))) may determine if the test measurement is valid for any available measurement type. For example, in an embodiment, the available measurement types may include local oxygen saturation, regional oxygen saturation, blood pressure, temperature, one or more EPS, respiration rate, respiratory effort, and PTT. If, at step 308, the test measurement is valid for one of these measurement types, then the sensor element or element combination used for taking the test measurement may be stored as a possible "best" sensor elements for that measurement type at step 310. If the test measurement is not valid for any desired measurement type, then a new element or element combination may be tested. To be a "valid" measurement for any available measurement type, the test measurement may have to meet one or more metric thresholds, such as signal quality and signal strength. In some embodiments, a valid test measurement may be determined by correlating the test measurement with one or more models representative of available measurement types. If the correlation exceeds some threshold correlation, then the test measurement may be classified as a valid measurement for that measurement type. In an embodiment, both model correlation and metric thresholds are used to determine valid measurements.

At step 312, sensor array 100 (FIG. 1(*a*)) or the monitor connected to sensor array 100 (e.g., monitor 14 (FIG. 1(*b*))) may determine if there are more sensor elements, element combinations, or both to test. For example, all sensor elements and/or element combinations may be tested. As another example, a user may set a threshold signal integrity metric for a given measurement type. After the threshold signal integrity has been met by a valid test measurement, a test specification may dictate that no further test measurements be made for that measurement type. In addition, as described above, test specifications may indicate a desired measurement frequency or absolute time a measurement of a particular type is needed (e.g., in order to be passed to another process). Thus, new sensor elements or element combinations may be automatically tested until a new measurement is needed by some other process or until a user stops the measurement test cycle. At step 314, the best sensor element or element combination may be outputted for each measurement type. For example, the best sensor element or element combination may be saved to memory, recorded to a storage device, logged to a file, displayed (e.g., on a monitoring system or display screen), or used for monitoring the corresponding measurement type.

The foregoing is merely illustrative of the principles of this disclosure and various modifications can be made by those skilled in the art without departing from the scope and spirit of the disclosure.

What is claimed is:

1. A method for determining one or more physiological parameters of a subject, the method comprising:
 receiving physiological signals from sensor elements coupled to the subject;
 analyzing, using a processor, the physiological signals using a first metric associated with a first physiological parameter;
 analyzing, using a processor, the physiological signals using a second metric associated with a second physiological parameter;
 identifying, using a processor, whether the first physiological parameter can be determined based at least in part on the first metric;
 identifying, using a processor, whether the second physiological parameter can be determined based at least in part on the second metric; and
 determining, using a processor, at least one of the first and second physiological parameters of the subject based at least in part on the physiological signals received from the sensor elements and based at least in part on whether the first and second physiological parameters can be determined.

2. The method of claim 1, further comprising:
 receiving an indication of a set of predefined measurement types; and
 identifying the first and second physiological parameters from the set.

3. The method of claim 1, wherein:
 analyzing the physiological signals using the first metric comprises:
  correlating the physiological signals with a first model for a first available measurement type; and
  determining whether the correlation between the physiological signals and the first model exceeds a threshold for the first available measurement type; and
 analyzing the physiological signals using the second metric comprises:
  correlating the physiological signals with a second model for a second available measurement type; and
  determining whether the correlation between the physiological signals and the second model exceeds a threshold for the second available measurement type.

4. The method of claim 1, wherein further comprising:
 analyzing the physiological signals using the first metric comprises:
  comparing the physiological signals to the first metric, and
  determining whether the physiological signals meet a threshold level for the first metric; and
 analyzing the physiological signals using the second metric comprises:
  comparing the physiological signals to the second metric, and
  determining whether the physiological signals meet a threshold level for the second metric.

5. The method of claim 4, further comprising identifying an optimal measurement type that can be determined from the physiological signals based on the comparisons of the physiological signals to the first and second metrics.

6. A system for determining one or more physiological parameters of a subject, the system comprising:
 a sensor interface capable of receiving physiological signals from sensor elements coupled to the subject; and
 a processor coupled to the sensor interface, wherein the processor is capable of:
  analyzing the physiological signals using a first metric associated with a first physiological parameter and a second metric associated with a second physiological parameter;
  identifying whether the first physiological parameter can be determined based at least in part on the first metric;
  identifying whether the second physiological parameter can be determined based at least in part on the second metric; and
  determining at least one of the first and second physiological parameters of the subject based at least in part on the physiological signals received from the sensor elements and on whether the first and second physiological parameters can be determined.

7. The system of claim 6, wherein the processor is further capable of:
 receiving an indication of a set of predefined measurement types; and
 identifying the first and second physiological parameters from the set.

8. The system of claim 6, wherein the processor is further capable of:
 correlating the physiological signals with first and second models for respective first and second available measurement types; and
 determining whether the respective correlations between the physiological signals and the first and second models exceed a threshold for at least one of the first and second available measurement types.

9. The system of claim 6, wherein the processor is further capable of:
 comparing the physiological signals to the first and second metrics; and determining whether the physiological signals meet at least one threshold level for the first and second metrics.

10. The system of claim 9, wherein the processor is further capable of identifying an optimal measurement type that can be determined based on the comparisons of the physiological signals to the first and second metrics.

\* \* \* \* \*